United States Patent [19]

Miano et al.

[11] Patent Number: 5,275,741
[45] Date of Patent: Jan. 4, 1994

[54] REACTOR FOR PHOTOOXIDATIONS IN AN AQUEOUS ENVIRONMENT

[75] Inventors: Fausto Miano, Enna; Enrico Borgarello, Turin, both of Italy

[73] Assignee: Eniricerche S.p.A., Milan, Italy

[21] Appl. No.: 958,468

[22] Filed: Oct. 8, 1992

Related U.S. Application Data

[63] Continuation of Ser. No. 807,758, Dec. 17, 1991, abandoned, which is a continuation of Ser. No. 521,357, May 8, 1990, abandoned.

[30] Foreign Application Priority Data

May 11, 1989 [IT] Italy ................. 20446 A/89
Jun. 30, 1989 [IT] Italy ................. 21038 A/89

[51] Int. Cl.$^5$ .................... C02F 1/32; C02F 1/68
[52] U.S. Cl. .................... 210/748; 210/763; 210/908
[58] Field of Search .......... 210/748, 763, 908; 422/186.3; 250/435; 502/350, 527; 204/155, 157.15, 158.2, 158.21

[56] References Cited

U.S. PATENT DOCUMENTS

| | | | |
|---|---|---|---|
| 2,189,279 | 2/1940 | Bitner | 210/748 |
| 3,642,912 | 2/1972 | Sharp et al. | 568/794 |
| 4,012,321 | 3/1977 | Koubek | 210/761 |
| 4,069,153 | 1/1978 | Gunther | 210/748 |
| 4,141,830 | 2/1979 | Last | 210/748 |
| 4,179,616 | 12/1979 | Coviello et al. | 210/748 |
| 4,274,970 | 6/1981 | Beitzel | 210/748 |
| 4,456,512 | 6/1984 | Bieler et al. | 210/748 |
| 4,571,290 | 2/1986 | Ward et al. | 204/157.69 |
| 4,788,038 | 11/1988 | Matsunaga | 210/748 |
| 4,849,115 | 7/1989 | Cole et al. | 210/748 |
| 4,857,204 | 8/1989 | Joklik | 210/748 |
| 4,861,484 | 8/1989 | Lichtin et al. | 210/748 |
| 4,863,608 | 9/1989 | Kawai et al. | 210/748 |
| 4,892,712 | 1/1990 | Robertson et al. | 210/763 |

FOREIGN PATENT DOCUMENTS

| | | | |
|---|---|---|---|
| PH7074 | 7/1987 | Australia | 210/763 |
| 0306301 | 3/1989 | European Pat. Off. | |
| 3245811 | 6/1983 | Fed. Rep. of Germany | |
| 60-61094 | 4/1985 | Japan | 210/763 |

OTHER PUBLICATIONS

Water Research, vol. 20, No. 5, pp. 569–578, May, 1986, R. W. Matthews, "Photo-Oxidation of Organic Material In Aqueous Suspensions of Titanium Dioxide".

Patent Abstracts of Japan, vol. 12, No. 258 (C-513), Jul. 20, 1988, & JP-A-63042793, M. Hosokawa, et al., "Method For Cleaning Fluid By Utilizing Titanium Oxide", Feb. 23, 1988.

*Primary Examiner*—Stanley S. Silverman
*Assistant Examiner*—Neil M. McCarthy
*Attorney, Agent, or Firm*—Oblon, Spivak, McClelland, Maier & Neustadt

[57] ABSTRACT

The object of the present invention is a method for the photocatalytic treatment of aqueous mixtures of polluting substances. Such a method consists in submitting such mixtures to irradiation in the presence of titanium dioxide while they are circulating inside a reactor formed by a hollow space of not more than 5 cm of thickness, whose inner wall is the wall of a lamp emitting at least a fraction of its radiations with a wavelength shorter than 400 nm.

In this reactor a cooling sheath is not provided between the lamp and the reaction mixture and temperature control is accomplished by means of the circulation of the same reaction mixture inside the reactor.

4 Claims, 2 Drawing Sheets

REACTOR FOR PHOTOOXIDATIONS IN AN AQUEOUS ENVIRONMENT

This application is a continuation of application Ser. No. 07/807,758, filed on Dec. 17, 1991, now abandoned, which is a continuation of application Ser. No. 07/521,357 filed on May 8, 1990 now abandoned.

BACKGROUND OF THE INVENTION

The present invention relates to a method for performing processes of heterogeneous photocatalysis, which process optimizes the exploitation of the radiations emitted by the light source and can be applied to large reaction volumes. Thanks to these features, the present method is highly interesting in particular for carrying out processes of heterogeneous photocatalysis on an industrial scale.

By now, a large number of photocatalytic processes in heterogeneous phase have been described in pertinent technical literature.

Such processes are characterized by the use as the catalyst, in aqueous media, of a semiconductor, such as, e.g., $TiO_2$, on whose surface the substance is adsorbed, which has to be transformed.

By irradiation with photons having a sufficiently high energy, the promotion of an electron from the "valency band" to the "conduction band" of semiconductor is carried out.

In that way, a separation of charges, denominated "electron-hole pair" is accomplished, which migrates to the interface between the liquid phase and the semiconductor, where it is capable of causing redox reactions on the adsorbed compounds.

Many chemical substances exist, which when are individually taken and are submitted to such a treatment undergo transformations: e.g., $CN^-$ and $SO_3^{2-}$, which are oxidated ([Bard, J. Phys. Chem. 1977–81 (1984)], organic acids, which are decarboxylated (Bard, J.A.C.S. 1978 100: 2239), hydrocarbon compounds, which undergo oxidation, atrazine, which is transformed into cyanuric acid.

Some substances in particular, under the hereinabove disclosed conditions, are completely mineralized, i.e., their skeleton of carbon atoms is completely converted into carbon dioxide. For example, aliphatic and aromatic halides, phenols and chlorophenols can be completely mineralized by means of heterogeneous photocatalysis [Pelizzetti, Serpone, Borgarello, Photocatalysis and Environment 467–497 M. Schiavello (Ed.) 1988]

Therefore, the great importance is evident, which such a type of reaction can have in the fight against the pollution of drinkwater and in general of aquatic environment.

In this regard, the decay due to the mineralization of, besides the hereinabove mentioned compounds, dichlorobenzenes, chloronitrobenzenes, polychlorobiphenyls and polychlorodioxines (Barbeni Chemosphere 15: 1913 1986) is known.

Such descriptions relate to processes accomplished on the laboratory scale, whilst their application on the industrial scale involves considerable problems as regards the equipment and the possibility of application to complex polluting mixtures.

DESCRIPTION OF THE PRIOR ART

As regards the first aspect, photochemical reactors of the "submerged-lamp" type are known. They substantially consist of a conventional chemical reactor in which a suitable lamp, as the source of photons, is inserted through the cover and is dipped in the reaction mixture, which contains the substance to be demolished and the catalyst.

This type of reactor suffers from the following drawbacks:

(a) A cooling jacket is necessary in order to prevent the lamp from overheating in case a high-pressure mercury-vapour or high-pressure xenon-vapour lamp is used.

Inside this jacket the precipitation of inorganic salts and the formation of seaweeds can occur. Thus, opaque regions are formed which, together with the effect of characteristic absorption of the glass the same jacket is made from, act as a shield and absorb a portion of photons, which are hence lost.

(b) The reactor is so designed, as to be able to contain the whole volume of the reaction mixture, and therefore is not so dimensioned as to match the geometry of the lamp, as well as of the irradiation region.

In fact, it is well-known that the distance inside the reaction mixture the photons are capable of traveling over before losing their energy is very short, and therefore the farthest away regions of the reactor are not reached by a large enough amount of radiations.

This latter drawback cannot be overcome even if stirring is provided.

Other types of reactors which can be used on an industrial scale are the annular reactor, the "Tarkoy-Campana" reactor and the "Braun-De Meijere reactor".

The first one is formed by two coaxial cylinders which bound the reaction region, with the lamp being arranged on the symmetry axis. In this case too, a cooling jacket is provided between the lamp and the reaction mixture.

In "Tarkoy-Campana" reactor, disclosed in U.S. Pat. No. 3,628,010, the geometry of the reaction region is optimized relatively to the dimensions and the length of the lamp. The same advantages are obtained by using the "Braun-De Meijere" reactor (A. M. Braun "Technologie photochimique" Presses Politechniques Romandes, Lausanne, 1986).

These last two types of photochemical reactor are very efficient, but in the particular case of photocatalytic reactions in heterogeneous phase they are difficult to be used, owing to the presence of suspended catalyst particles in the reaction mixture.

SUMMARY OF THE INVENTION

The present Applicant has found now a reactor for heterogeneous photocatalysis, which is characterized by the absence of the cooling jacket between the lamp and the reaction mixture. The reactor consists of a hollow space, whose inner wall is the wall of a lamp which emits at least one fraction of its radiations with a wavelength shorter than 400 nm, and preferably comprised within the range of from 320 to 370 nm.

Temperature control is obtained by causing the reaction mixture to continuously circulate through said hollow space.

Figure 1:
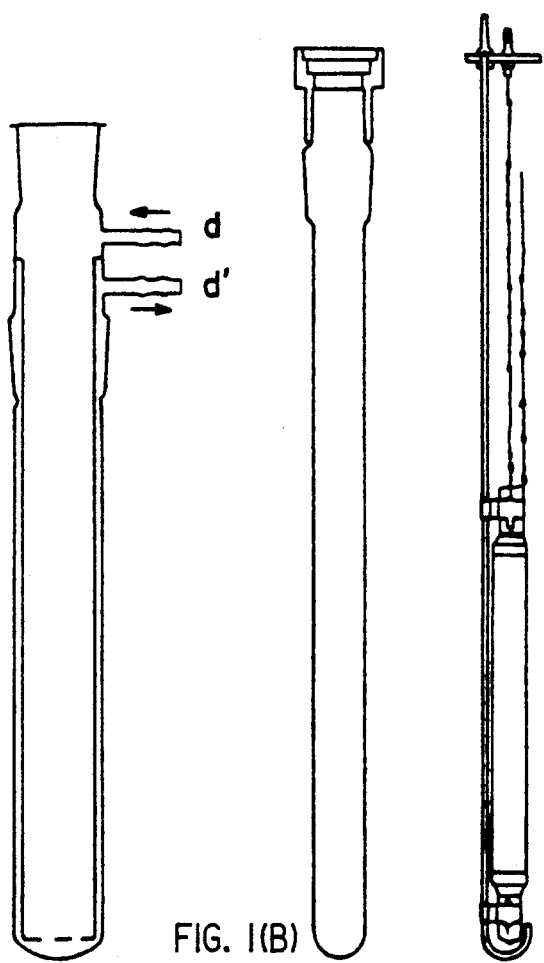
In FIG. 1 the components of the reactor, and the lamp are shown: A is the outer wall of the reactor, and B is the container of the lamp C.

By sliding B into A and connecting them by means of a conical fitting, the jacket is formed, inside which the reaction mixture circulates; d and d' indicate the inlet and the outlet ways for the reaction mixture.

When such a type of reactor is used, the loss of photons can be avoided, which is due to absorption both by the opaque regions formed by the precipitation of inorganic salts, or owing to the growth of seaweeds, as well as to absorption by the glass walls normally existing between the lamp and the reaction mixture.

Furthermore, with this reactor large amounts of solutions can be processed, without the risk—as it occurs in the reactor of submerged-lamp type—that reactor regions, and therefore regions of the reaction mixture, are too far away from the lamp, and therefore cannot be reached by the light emitted by the lamp.

The lamps useable in the "jacket" reactor which is the object of the present invention are high-pressure mercury-vapour or high-pressure xenon-vapour arc lamps.

The jacket reactor has a width of not more than 5 cm, and preferably not higher than 2.5 cm. It substantially consists of a sheath inside which the reaction mixture flows.

Inside this sheath baffles can be installed, which generate an obliged path for the reaction mixture, increasing the stay time thereof inside the interior of the reactor, so as to favour the interaction of said reaction mixture with the photons generated by the lamp.

The reaction mixture is caused to flow through this sheath with a flowrate which is computed on the basis of the power of the lamp, with said power being expressed as watts, and therefore obtaining how much aqueous mixture is necessary in order to exchange such a heat amount (it is therefore assumed that the coefficient of heat exchange of the reaction mixture is the same as of water). On the basis of the results which one wishes to obtain, a reaction mixture will be exposed to irradiation by being caused to flow a plurality of times through the jacket reactor. This result can be accomplished by connecting with the reactor a tank containing the reaction mixture and equipped with a pump which secures a continuous recycle of the reaction mixture between the reactor and the tank.

The same results as of the preceding "batchwise" system can be obtained by operating in continuous with a long enough lamp, or with a plurality of lamps arranged in cascade.

A set of tests were carried out using for exemplifying purposes a jacket reactor of 100 ml of volume, and a mercury-vapour lamp with a specific power of 40 W/cm and an useful length of 3 cm.

100 ml of a mixture containing 50 ppm of o-nitrophenol and 1 g of $TiO_2$/Litre dispersed in water were charged to this reactor.

This is a reference test, in which the volume of solution submitted to the treatment of photocatalysis was equal to the volume of the reactor, and therefore, inasmuch as a circulation of the reaction mixture did not take place, an external cooling had to be applied.

The data resulting from this test indicates the better reaction yield which can be obtained when the cooling sheath is eliminated.

After 60 minutes of irradiation, the solution resulted to contain 14.6 ppm of unreacted product, whilst the residual amount was decomposed up to mineralization.

A test under similar conditions was carried out on 500 ml of the above mixture.

In this case, the reactor of 100 ml of capacity was connected with a tank which contained the residual portion of the reaction mixture.

The circulation of the reaction mixture between the reactor and the tank was obtained by means of a pump, and in this way the cooling of the lamp was secured.

After 60 minutes, the concentration was decreased from 50 ppm to 16 ppm. In other terms, it was possible to process a volume which is 5 times as large as the volume treated in the reference test, with the decomposition rate remaining constant. In order to reach the threshold of loss of efficiency of this reactor, a volume 10 times as large as the volume treated in the reference test had to be processed, In fact, when 1 litre of reaction mixture containing 50 ppm of ortho-nitrophenol and 1 g of $TiO_2$/litre was submitted to irradiation, after 60 minutes a concentration of 24 ppm was obtained.

The results which can be obtained with the "jacket" reactor according to the present invention considerably improve if into the reaction mixture air is injected.

As the reference test, 200 ml of a mixture containing 50 ppm of o-nitrophenol and 1 g of $TiO_2$/litre was submitted to a treatment of heterogeneous photocatalysis inside a jacket reactor of 200 ml of volume, equipped with a lamp with a specific power of 40 W/cm and an useful length of 3 cm. Air was injected into the interior of the reactor. Also in this case, inasmuch as the reaction mixture was not circulated, an external cooling was applied. With this test, the results were evaluated, which can be obtained with a "jacket" reactor, i.e., without the hollow space of the cooling jacket, when into the reaction mixture air is injected.

After 30 minutes of irradiation, only 9.2 ppm of o-nitrophenol had remained, which decreased down to less than 1 ppm after 60 minutes.

The volume of the reaction mixture to be processed was then increased to a 2.5 times larger volume. 500 ml of this reaction mixture was submitted to irradiation inside the same reactor, which this time was connected with a suitable tank and a pump in order to secure the continous circulation of the reaction mixture through the system.

Air can be injected into the reaction circuit indifferently at reactor level, and at tank level.

From this second test, the same results were obtained again, which were obtained from the reference test: after 30 minutes, the concentration decreased down to 8.8 ppm, and after 60 minutes it was lower than 1 ppm.

For comparison purposes, 1.6 l of the same solution was processed in the presence of 1 g of $TiO_2$/litre and under a stream of air, in a reactor of submerged-lamp type, equipped with a 1000-W lamp, therefore extremely powerful, whose cooling was secured by means of a suitable cooling jacket.

After 60 minutes of treatment, the solution resulted to contain still 25 ppm of o-nitrophenol.

The same result was obtained when a solution of 50 ppm of chlorophenol was submitted to irradiation under similar conditions.

This worsening observed in the results is to be attributed both to the cooling jacket acting as a shield for photons generated by the lamp, and to the relatively large reaction volume, which does not enable a homogeneous irradiation of the whole mixture to be obtained.

Therefore, the present Applicant has discovered a method for performing processes of photocatalysis and of heterogeneous photocatalysis, which comprises the use of a reactor formed by a hollow space whose inner wall is the wall of a lamp which emits at least a fraction of its radiations with a wavelength shorter than 400 nm. The reaction mixture containing the substance to be demolished, in the presence of titanium dioxide as the catalyst, is caused to continuously circulate inside said hollow space.

According to the results which one wants to obtain, the treatment of photocatalysis will be prolonged by causing said reaction mixture to flow a plurality of times through the "jacket" reactor.

This result is achieved by connecting the reactor with a suitable tank and securing the proper circulation of the reaction mixture through the reactor and the tank by means of a suitable pump. As an alternative, the same results can be achieved by eliminating the tank, and operating in continuous mode by means of a long enough lamp, or of a plurality of lamps installed in series: in both cases, the reactors shall be so dimensioned as to be adapted to the geometry and length of the lamps.

The method found by the present Applicant shows the following advantages:

(a) the light emitted by the lamp is better exploited, without photons getting lost owing to the absorption by a cooling jacket; therefore, the reaction yield is maximized.

The temperature of the lamp is controlled by the same reaction mixture, which is made circulate in continuous.

(b) This instant system can be applied to large reaction volumes, with the treatment yields being kept constant. With the "submerged-lamp" reactors according to the prior art, an increase in volume causes a decrease in reaction yield.

The method according to the present invention can be advantageously used in the field of the fight against environmental pollution, in order to purify drinkwaters and natural waters from both organic and inorganic pollutants, such as fungicides, herbicides, cyanides, and so forth.

Such a method can be applied as well to complex mixtures of organic and inorganic compounds, such as those mixtures which are found in waste waters from chemical factories, zootechnical factories, and so forth.

In this regard, a complex mixture of organic compounds deriving from the waste liquors from a chemical factory was submitted to a process of heterogeneous photocatalysis carried out inside a "jacket" reactor. Before being submitted to said treatment, this mixture was characterized by a COD (Chemical Oxygen Demand) of 54 mg of $O_2$ per litre. After a 5-hours-long treatment of 1000 ml of such a mixture in the presence of 1 g of $TiO_2$/litre, and with a lamp with a specific power of 40 W/cm and an useful length of 3 cm, inside a jacket reactor of 100 ml of capacity connected with a suitable tank and equipped with a pump which caused the reaction mixture to continuously circulate, a COD lower than 10 mg/l of $O_2$ was measured.

Equally satisfactory results were obtained when the waste liquors coming from a pig-breeding factory were submitted to a photocatalytic treatment.

In particular, 500 ml of a mixture with a COD of 320 mg of $O_2$/l were irradiated by means of two lamps in cascade, each of which has a specific power of 40 W/cm and a length of 3 cm. After 4 hours of irradiation, COD value resulted to be of 84 mg of $O_2$/litre.

The method according to the present invention can hence be indifferently applied to solutions containing one compound only, or to complex mixtures of organic or inorganic compounds.

As the catalyst in the process according to the present invention $TiO_2$ powder is used which, once added to the polluted solutions, forms colloidal suspensions or solutions; or $TiO_2$ is used in the form of microspheres.

In case $TiO_2$ powder is used, the catalyst is recovered at the end of the process by decantation or centrifugation. The resulting liquors contain less than 1 mg of $TiO_2$/litre, can be disposed of to the environment, but they are not drinkwater.

Therefore, a preferred aspect of the instant invention is submitting aqueous solutions of pollutant substances to a photocatalytic treatment inside the hereinabove disclosed reactor, using microspheres of $TiO_2$ of diameter comprised within the range of from 0.1 to 5.0 mm as the catalyst, under such flowing conditions as to generate a fluidized bed of catalyst. In such a way, the catalyst remains always inside the reactor and after the photocatalytic treatment no further steps of purification of the resulting liquors are necessary any longer in order to recover the catalyst and render said liquors pure enough in order it to be disposed of to the environment.

Furthermore, owing to the fact that the catalyst remains confined inside the reactor, the probability that said catalyst is reached by the light radiations increases, with the probability that the pollutant substances adsorbed on said catalyst surface are demolished consequently increasing.

Furthermore, the microspheres of $TiO_2$ show a mechanical strength by far higher than of the catalysts based on supported titanium dioxide, e.g., on glass.

In fact, these latter, owing to the rubbing they undergo, tend to crumble and to release $TiO_2$ powder which, at the end of the process, causes the above mentioned separation problems.

It should be finally stressed that the useful life time of this microsphere catalyst is very high: in fact, possible substances tending to accumulate on $TiO_2$ surface can be removed by means of a sufficient irradiation, and do not modify its reactivity.

Therefore, a preferred aspect of the present invention is a method for the photocatalytic treatment, in the presence of titanium dioxide, of aqueous mixtures of pollutants, which consists in submitting said mixtures to irradiation while they are caused to circulate inside a reactor formed by a hollow space of thickness of not more than 5 cm, whose inner wall is the wall of a lamp emitting at least a fraction of its radiations with a wavelength shorter than 400 nm, which method is characterized in that according to it $TiO_2$ in the form of microspheres with a diameter comprised within the range of from 0.1 to 5.0 mm is used, which microspheres are kept moved inside the interior of the reactor by the flowing stream of the reactant mixture, but without being removed.

$TiO_2$ microspheres which can be used in the process according to the present invention are those prepared according to U.K. Patent No. 2.112.764 by mixing a titanium halide and an alcohol in order to yield an alcoholic solution of the corresponding organometallic titanium compound, thickening said solution by adding an organic polymer to it, then subdividing it by means of an atomizer into liquid droplets which are immediately solidified into gel particles by contact with an alcoholic solution of alkali; the gel particles are then dried or calcined.

$TiO_2$ prepared according to UK 2.112.764 has a specific surface area of 150 $m^2/g$ vs. the specific surface area of 50 $m^2/g$ of $TiO_2$ powder and of 0.5 $m^2/g$ of glass supported $TiO_2$: its use in a photocatalytic process favours a better contact between the catalyst and the mixture of pollutant substances.

The method according to the present invention, in its preferred aspect according to which the catalyst is constituted by $TiO_2$ microspheres, can be carried out either continuously or batchwise.

Figure 2:
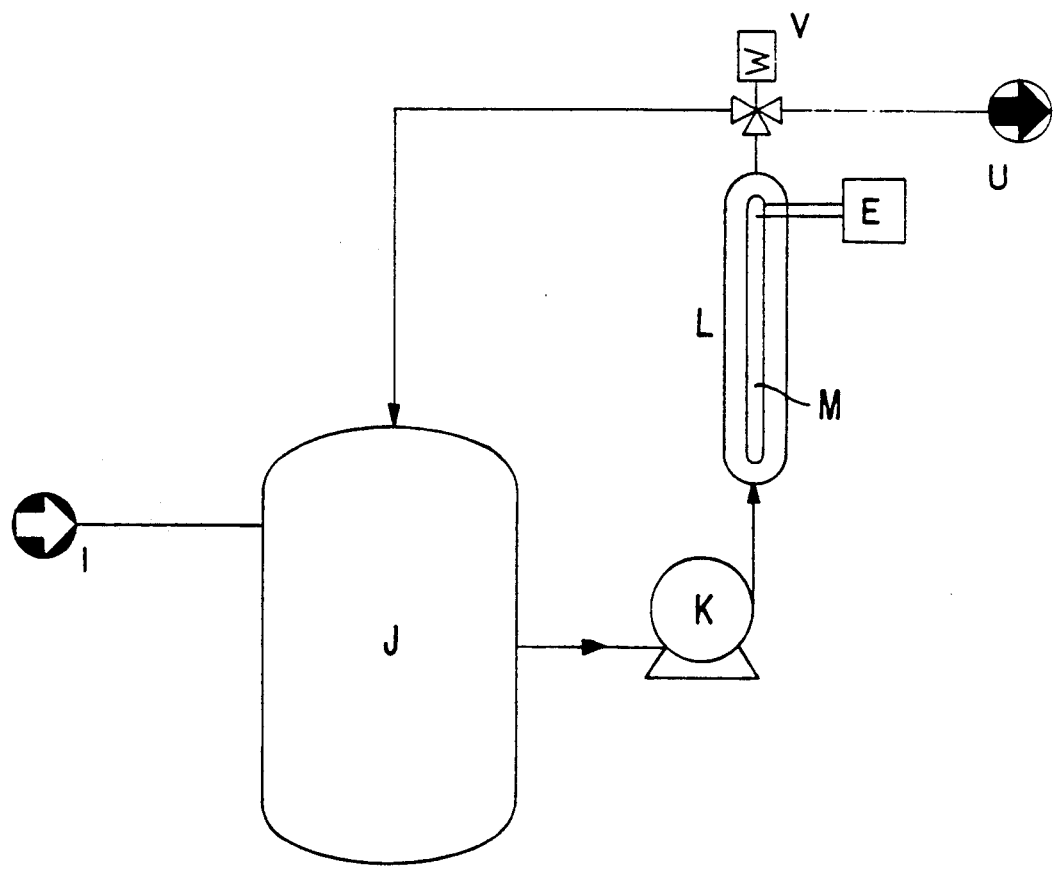
FIG. 2 shows a facility for treating an o-nitrophenol solution according to the method of the invention.

A possible relization of the first case is shown in FIG. 2: the reaction mixture is fed through the inlet I to the tank J, and from this latter it is charged to the reactor L by means of the pump K. Inside the reactor the reaction mixture undergoes the irradiation, in the presence of the microspheres of titanium dioxide, by the lamp M, powered by the electrical generator E. From the outlet U, controlled by the electrovalve V, an aliquot of the reaction mixture at the desired concentration is discharged, with the remainder portion of said reaction mixture being recycled to the tank.

The batchwise process can be accomplished according to a process scheme analogous to the preceding one, with the difference that all of the mixture to be purified is contained inside the tank J and is circulated through the reactor L so as to be submitted a plurality of times to the irradiation, until the desired concentration of pollutant substances is reached. By operating according to the continuous mode, the following advantages are achieved:

1) the dead times required by the discharge and feed restoration are eliminated; and
2) also polluting mixtures with a so high pollutant concentration as not to meet the optimum conditions to have mineralization can be used. In fact, in the steady state, the volume of mixture of pollutant substances entering the tank at each time is diluted by the already contained mixture, yielding such a concentration that, by means of one pass through the reactor, the desired end concentration is reached.

In the following some Examples of application of the method according to the present invention in its preferred aspect in which the catalyst is constituted by microspheres of $TiO_2$ are reported.

EXAMPLE 1

500 ml of an aqueous mixture containing 50 ppm of o-nitrophenol is submitted to photooxidation in the presence of 10 g of $TiO_2$ microspheres inside a jacket-reactor similar to the hereinabove disclosed reactors, of 2.5 mm of thickness, equipped with a high-pressure mercury-vapours lamp of 125 W and installed in a batchwise-operating facility.

The mixture is first circulated 15 minutes in the darkness, so that the surface of the catalyst gets saturated by the pollutant substances. A concentration of the solution of 37 ppm is thus obtained, and then the irradiation is carried out.

In the following table the obtained results are reported:

| Time (minutes) | Concentration (ppm) |
| --- | --- |
| 0 | 37 |
| 30 | 11 |
| 60 | 4 |

At the end of the reaction the amount of produced $CO_2$ was determined, and resulted to be of 1 mmol.

EXAMPLE 2

500 ml of an aqueous mixture of o-nitrophenol is treated in the same way as disclosed in Example 1 inside a jacket-reactor of 5.0 mm of thickness, equipped with a low-pressure mercury-vapours lamp of 40 W, in the presence of 40 g of $TiO_2$ microspheres.

The results obtained are reported in the following table:

| Time (minutes) | Concentration (ppm) |
| --- | --- |
| 0 | 37 |
| 30 | 29 |
| 60 | 22 |
| 120 | 15 |
| 240 | 5 |

EXAMPLE 3

500 ml of an aqueous mixture deriving from the waste liquors from a pig-breeding factory is submitted to photooxidation in the presence of 10 g of $TiO_2$ as microspheres inside a reactor like the one disclosed in Example 1, equipped with two high-pressure mercury-vapours lamps of 120 W. Before undergoing the treatment, the mixture showed a values of COD (Chemical Oxygen Demand, code IRSA E007) of 300 mg of $O_2$/liter. After a 4-hours treatment COD value has decreased down to 157 mg of $O_2$/liter, and after 6 hours it was of 68 mg of $O_2$/liter.

EXAMPLE 4

1000 ml of an aqueous mixture deriving from the waste liquors from a chemical industry was submitted to photooxidation under the same conditions as disclosed in the preceding Example. The so obtained results are reported in the following Table:

| Time (hours) | Concentration (mg/l of $O_2$) |
| --- | --- |
| 0 | 47 |
| 6 | <10 |

EXAMPLE 5

500 ml of an aromatics-containing aqueous mixture was treated in the same way as disclosed in Example 2. The results obtained are reported in the following

| Time (hours) | Concentration (mg/l of $O_2$) |
| --- | --- |
| 0 | 90 |
| 2 | 72 |

-continued

| Time (hours) | Concentration (mg/l of O$_2$) |
| --- | --- |
| 8 | 35 |

EXAMPLE 6

In a facility like the one depicted in FIG. 2, a solution containing 50 ppm of o-nitrophenol is fed to the tank A at a flowrate of 100 ml/hour.

The tank has a volume of 1000 ml, the reactor has a thickness of 5 mm and the lamp, a low-pressure mercury-vapour one, has a power of 40 W.

From the outlet U 100 ml/hour of treated solution containing 9 ppm of polluting substance is discharged.

We claim:

1. In a method for the photocatalytic treatment with titanium dioxide of aqueous mixtures of pollutants, wherein said mixtures are subjected to irradiation while circulating within a reactor formed by a hollow space of thickness of not more than 5 cm, the inner wall of said jacket being the outer wall of a lamp emitting radiation having a wavelength less than 400 nm, the improvement comprises: that the titanium dioxide is in the form of microspheres having a diameter of from 0.1 mm to 5.0 mm and that said microspheres are retained within said jacket and stirred by the flow of said mixtures, said microspheres prepared by
   (a) preparing an alcoholic solution of an organometallic compound of titanium;
   (b) optionally thickening said solution by the addition of an organic polymer;
   (c) subdividing the solution into droplets which are solidified into gel particles by contact with an alkaline solution in an anhydrous environment, or in an environment with a controlled water content;
   (d) drying and/or calcining the gel particles to form said microspheres.

2. The method of claim 1, in which said lamp emits at least a fraction of its radiation at a wavelength within the range of 320 to 380 nm.

3. The method of claim 1, in which said lamp is a high-pressure mercury vapor or high-pressure xenon vapor arc lamp.

4. The method of claim 1 in which air or oxygen is injected into the aqueous mixture of pollutants.

* * * * *